US011919950B2

(12) United States Patent
Adams et al.

(10) Patent No.: US 11,919,950 B2
(45) Date of Patent: Mar. 5, 2024

(54) EXPRESSION VECTOR ENCODING ANTIBODY MOLECULE WHICH BINDS IL-17A AND IL-17F

(71) Applicant: UCB BIOPHARMA SRL, Brussels (BE)

(72) Inventors: Ralph Adams, Slough (GB); Terence Seward Baker, Slough (GB); Alastair David Griffiths Lawson, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 400 days.

(21) Appl. No.: 17/122,752

(22) Filed: Dec. 15, 2020

(65) Prior Publication Data

US 2021/0309734 A1 Oct. 7, 2021

Related U.S. Application Data

(60) Continuation of application No. 15/974,407, filed on May 8, 2018, now abandoned, which is a continuation of application No. 14/690,892, filed on Apr. 20, 2015, now Pat. No. 9,988,446, which is a division of application No. 14/074,880, filed on Nov. 8, 2013, now Pat. No. 9,034,600, which is a division of application No. 13/348,456, filed on Jan. 11, 2012, now Pat. No. 8,580,265.

(60) Provisional application No. 61/432,814, filed on Jan. 14, 2011.

(51) Int. Cl.
C12N 15/09 (2006.01)
C07K 16/24 (2006.01)

(52) U.S. Cl.
CPC ........ C07K 16/244 (2013.01); *C07K 2317/33* (2013.01); *C07K 2317/92* (2013.01)

(58) Field of Classification Search
CPC .. C12N 15/63; C07K 16/244; C07K 2317/33; C07K 2317/56
See application file for complete search history.

(56) References Cited

U.S. PATENT DOCUMENTS

| | | |
|---|---|---|
| 4,741,900 A | 5/1988 | Alvarez et al. |
| 4,946,778 A | 8/1990 | Ladner et al. |
| 5,219,996 A | 6/1993 | Bodmer et al. |
| 5,223,409 A | 6/1993 | Adner et al. |
| 5,403,484 A | 4/1995 | Adner et al. |
| 5,427,908 A | 6/1995 | Dower et al. |
| 5,516,637 A | 5/1996 | Huang et al. |
| 5,571,698 A | 11/1996 | Ladner et al. |
| 5,580,717 A | 12/1996 | Dower et al. |
| 5,585,089 A | 12/1996 | Queen et al. |
| 5,658,727 A | 8/1997 | Barbas et al. |
| 5,667,425 A | 9/1997 | Pineau et al. |
| 5,698,426 A | 12/1997 | Huse |
| 5,733,743 A | 3/1998 | Johnson et al. |
| 5,750,753 A | 5/1998 | Kimae et al. |
| 5,780,225 A | 7/1998 | Wigler et al. |
| 5,821,047 A | 10/1998 | Garrard et al. |
| 5,969,108 A | 10/1999 | McCafferty et al. |
| 6,274,711 B1 | 8/2001 | Golstein et al. |
| 7,790,163 B2 | 9/2010 | Jaspers et al. |
| 8,580,265 B2 | 11/2013 | Adams et al. |
| 9,988,446 B2 | 6/2018 | Adams et al. |
| 2007/0160576 A1 | 7/2007 | Arnott et al. |
| 2008/0181888 A1 | 7/2008 | Ambrose et al. |

FOREIGN PATENT DOCUMENTS

| | | |
|---|---|---|
| EP | 0392745 A2 | 10/1990 |
| EP | 0948544 A1 | 10/1999 |
| WO | 86/01533 A1 | 3/1986 |
| WO | 89/00195 A1 | 1/1989 |
| WO | 89/01476 A1 | 2/1989 |
| WO | 90/02809 A1 | 3/1990 |
| WO | 91/09967 A1 | 7/1991 |
| WO | 91/10737 A1 | 7/1991 |
| WO | 91/16353 A1 | 10/1991 |
| WO | 92/01047 A1 | 1/1992 |
| WO | 92/02551 A1 | 2/1992 |
| WO | 92/18619 A1 | 10/1992 |
| WO | 92/22583 A2 | 12/1992 |
| WO | 93/06231 A1 | 4/1993 |
| WO | 93/08829 A1 | 5/1993 |
| WO | 93/11236 A1 | 6/1993 |
| WO | 93/22853 A1 | 11/1993 |
| WO | 95/15982 A2 | 6/1995 |
| WO | 95/20401 A1 | 8/1995 |
| WO | 97/04097 A2 | 2/1997 |
| WO | 98/20734 A1 | 5/1998 |
| WO | 98/25971 A1 | 6/1998 |
| WO | 99/37779 A1 | 7/1999 |
| WO | 00/69463 A1 | 11/2000 |
| WO | 03/31581 A2 | 4/2003 |
| WO | 03/72036 A2 | 9/2003 |

(Continued)

OTHER PUBLICATIONS

Adair, J.R., & Lawson, A.D.G., "Therapeutic antibodies", Drug Design Reviews—Online, vol. 2, No. 3, pp. 209-217, 2005.

(Continued)

*Primary Examiner* — Dong Jiang
(74) *Attorney, Agent, or Firm* — MARSHALL, GERSTEIN & BORUN LLP

(57) ABSTRACT

The invention relates to antibody molecules having specificity for antigenic determinants of both IL-17A and IL-17F, therapeutic uses of the antibody molecules and methods for producing said antibody molecules.

8 Claims, 7 Drawing Sheets

Figure 7:
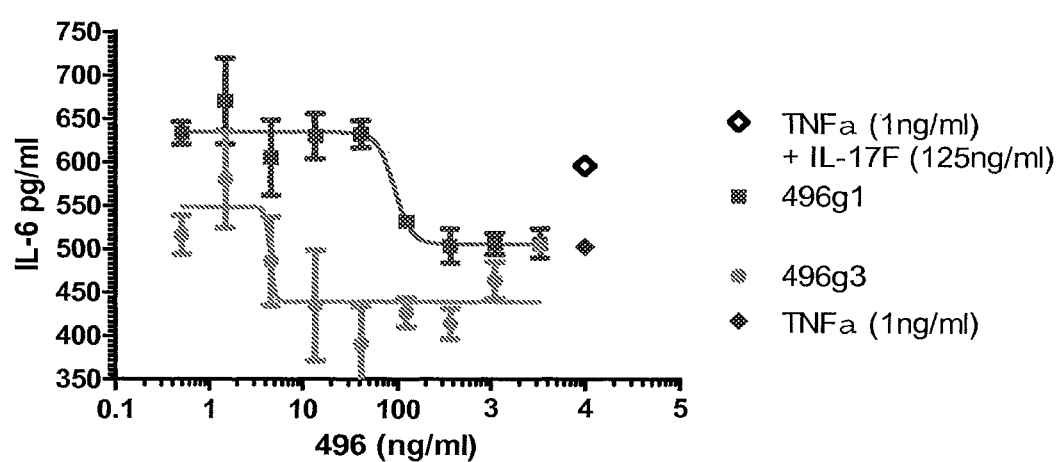

Specification includes a Sequence Listing.

(56) References Cited

FOREIGN PATENT DOCUMENTS

| WO | 2004/051268 A1 | 6/2004 |
|---|---|---|
| WO | 2004/072116 A2 | 8/2004 |
| WO | 2004/106377 A1 | 12/2004 |
| WO | 2005/003169 A2 | 1/2005 |
| WO | 2005/003170 A2 | 1/2005 |
| WO | 2005/003171 A2 | 1/2005 |
| WO | 2005/010044 A2 | 2/2005 |
| WO | 2005/051422 A1 | 6/2005 |
| WO | 2005/113605 A1 | 12/2005 |
| WO | 2005/117984 A2 | 12/2005 |
| WO | 2006/013107 A1 | 2/2006 |
| WO | 2006/054059 A1 | 5/2006 |
| WO | 2006/088833 A2 | 8/2006 |
| WO | 2006/088925 A2 | 8/2006 |
| WO | 2007/070750 A1 | 6/2007 |
| WO | 2007/106769 A2 | 9/2007 |
| WO | 2007/149032 A1 | 12/2007 |
| WO | 2008/001063 A1 | 1/2008 |
| WO | 2008/021156 A2 | 2/2008 |
| WO | 2008/047134 A2 | 4/2008 |
| WO | 2008/067223 A2 | 6/2008 |
| WO | 2008/121865 A1 | 10/2008 |
| WO | 2008/133684 A1 | 11/2008 |
| WO | 2008/134659 A2 | 11/2008 |
| WO | 2009/040562 A1 | 4/2009 |
| WO | 2009/130459 A2 | 10/2009 |
| WO | 2009/136286 A2 | 11/2009 |
| WO | 2010/025400 A2 | 3/2010 |
| WO | 2010/035012 A1 | 4/2010 |
| WO | 2011/030107 A1 | 3/2011 |
| WO | 2011/061492 A2 | 5/2011 |
| WO | 2011/086091 A1 | 7/2011 |

OTHER PUBLICATIONS

Ames, R.S., et al., "Conversion of murine Fabs isolated from a combinatorial phage display library to full length immunoglobulins", J. Immunol. Methods, vol. 184, No. 2, pp. 177-186, 1995.
Angal, S., et al. "A single amino acid substitution abolishes the heterogeneity of chimeric mouse/human (IgG4) antibody", Molecular Immunology, vol. 30, No. 1, pp. 105-108, 1993.
Babcook, J., et al., "A novel strategy for generating monoclonal antibodies from single, isolated lymphocytes producing antibodies of defined specificities", Proc. Natl. Acad. Sci. USA, vol. 93, No. 15, pp. 7843-7848, 1996.
Benchetrit et al. Interleukin-17 inhibits tumor cell growth by means of a T-cell-dependent mechanism. Blood, Mar. 15, 2002, vol. 99, No. 6, pp. 2114-2121.
Boder, et al., "Directed Evolution of Antibody Fragments with Monovalent Femtomolar Antigen-Binding Affinity", Proceedings of the National Academy of Sciences of USA, vol. 97, No. 20, pp. 10701-10705, 2000.
Brinkman, U., et al., "Phage Display of Disulfide-Stabilized FV Fragments", J. Immunol. Methods, vol. 182, No. 1, pp. 41-50, 1995.
Burchill, et al., "Inhibition of Interleukin-17 Prevents the Development of Arthritis in Vaccinated Mice Challenged with Borrelia burgdorferi", Infection and Immunity, vol. 71, No. 6, pp. 3437-3442, 2003.
Burton, et al., "Human Antibodies from Combinatorial Libraries", Advances in Immunology, vol. 57, pp. 191-280, 1994.
Chabaud, M. et al., "Contribution of Interleukin 17 to Synovium Matrix Destruction in Rheumatoid Arthritis", Cytokine, Academic Press Ltd., vol. 12, No. 7, pp. 1092-1099, 2000.
Chan et al., IL-23 stimulates epidermal hyperplasia via TNF and IL-20R2-dependent mechanisms with implications for psoriasis pathogenesis. J. Exp. Med. 203(12): 2577-87 (2006).
Chapman, "PEGylated Antibodies and Antibody Fragments for Improved Therapy: A Review", Advanced Drug Delivery Reviews, vol. 54, pp. 531-545, 2002.

Chothia, C. and Lesk, A.M., Canonical Structures for the Hypervariable Regions of Immunoglobulins, J. Mol. Biol., vol. 196, pp. 901-917, 1987.
Chung et al., "CD4 + T Cells Regulate Surgical and Postinfectious Adhesion Formation", The Journal of Experimental Medicine, vol. 195, No. 11, pp. 1471-1478, 2002.
Crameri, A., et al., "DNA Shuffling of a Family of Genes from Diverse Species. Accelerates Directed Evolution", Nature, vol. 391, pp. 288-291, 1998.
Davies, J et al., "Affinity Improvement of Single Antibody VH Domains: Residues in all Three Hypervariable Regions Affect Antigen Binding", Immunotechnology, Elsevier Science Publishers BV, vol. 2, No. 3, pp. 169-179, 1996.
Dubowchik, G.M., et al., "Receptor-mediated and enzyme-dependent targeting of cytotoxic anticancer drugs", Pharmacology and Therapeutics, vol. 83, No. 2, pp. 67-123, 1999.
Dumont, "IL-17 Cytokine/Receptor Families: Emerging Targets for the Modulation of Inflammatory Responses", Expert Opinion of Therapeutic Patents, Ashley Publications, GB, vol. 13, No. 3, pp. 287-303, 2003.
Fan et al. The prevalence of Th17 cells in patients with acute myeloid leukemia. Zhonghua Xue Ye Xue Za Zhi. Sep. 2010;31(9):617-620 (abstrac).
Gaffen, S.L., "An overview of IL-17 function and signaling", Cytokine, vol. 43, No. 3, pp. 402-407, 2008.
Harris, R.J., "Processing of C-terminal lysine and arginine residues of proteins isolated from mammalian cell culture", Journal of Chromatography, vol. 705, No. 1, pp. 129-134, 1995.
Hellings, et al., "Interleukin-17 Orchestrates the Granulocyte Influx into Airways After Allergen Inhalation in a Mouse Model of Allergic Asthma", American Journal of Respiratory Cell and Molecular Biology, vol. 28, pp. 42-50, 2003.
Hieter, P.A., et al., "Evolution of Human Immunoglobulin KJ Region Genes", J. Biol. Chem., vol. 257, No. 3, pp. 1516-1522, 1982.
Hoet, et al., "Generation of High-Affinity Human Antibodies by Combining Donor-Derived and Synthetic Complementarity-Determining-Region Diversity", Nature Biotechnology, vol. 23, No. 3, pp. 344-348, 2005.
Holliger, P., and Hudson, p. J., "Engineered antibody fragments and the rise of single domains", Nature Biotechnology, vol. 23, No. 9, pp. 1126-1136, 2005.
Holt, L. J., "Domain Antibodies: Proteins for Therapy", Trends in Biotechnology, Elsevier Publications, Cambridge, GB. vol. 21, No. 11, pp. 484-490, 2003.
International Search Report and Written Opinion issued for PCT/GB2012/050050, dated Apr. 12, 2012.
Kashmiri, S.V.S., et al., "SDR grafting-a new approach to antibody humanization, "Methods, vol. 36, pp. 25-34, 2005.
Kettleborough, C.A., et al., "Isolation of tumor cell-specific single-chain Fv from immunized mice using phage-antibody libraries and the reconstruction of whole antibodies from these antibody fragments", Eur. J. Immunol., vol. 24, No. 4, pp. 952-958, 1994.
Kohler, G. & Milstein, C., "Continuous cultures of fused cells secreting antibody of predefined specificity", Nature, vol. 256, pp. 495-497, 1975.
Korn, T., et al., "IL-17 and Th17 Cells", Annu. Rev. Immunol., vol. 27 pp. 485-517, 2009.
Kotake, et al., "IL-17 in Synovial Fluids from Patients with Rheumatoid Arthritis is a Potent Stimulator of Osteoclastogenesis", The Journal of Clinical Investigation, vol. 103, No. 9, pp. 1345-1352, 1999.
Kozbor, D., et al., "The production of monoclonal antibodies from human lymphocytes", Immunology Today, vol. 4, No. 3, pp. 72-79, 1983.
Low, et al., "Mimicking somatic hypermutation: affinity maturation of antibodies displayed on bacteriophage using a bacterial mutator strain", J. Mol. Biol., vol. 260, pp. 359-368, 1996.
Marks, et al., "By-passing Immunization Human: Building High Affinity Human Antibodies by Chain Shuffling", Bio/Technology, vol. 10, pp. 779-783, 1992.

(56) References Cited

OTHER PUBLICATIONS

Matsuzaki et al. Interleukin-17 as an effector molecule of innate and acquired immunity against infections. Microbiol Immunol., 2007; 51(12):1139-47.
Milstein, et al., "Hybrid Hybridomas and Their Use in Immunohistochemistry", Nature, vol. 305, pp. 537-539, 1983.
Moseley, T.A., et al., "Interleukin-17 family and IL-17 receptors", Cytokine Growth Factor Rev., vol. 14, No. 2, pp. 155-174, 2003.
Muranski et al. Tumor-specific Th17-polarized cells eradicate large established melanoma. Blood, 2008, 112: 362-373.
Numasaki, et al., "Interleukin-17 Promotes Angiogenesis and Tumor Growth", Blood, vol. 101, No. 7, pp. 2620-2627, 2003.
Pascalis, et al., "Grafting of "Abbreviated" Complementarity-Determining Regions Containing Specificity-Determining Residues Essential for Ligand Contact to Engineer a Less Immunogenic Humanized Monoclonal Antibody", Journal of Immunology, vol. 169, pp. 3076-3084, 2002.
Patten, P., et al., "Applications of DNA shuffling to pharmaceuticals and vaccines,", Curr. Opin. Biotechnol., vol. 8, No. 6, pp. 724-733, 1997.
Paul, W. E., "Structure and Function of Immunoglobulins", Fundamental Immunology, Raven Press, $3^{rd}$ Edition, pp. 292-295, 1993.
Persic, L., et al., "An integrated vector system for the eukaryotic expression of antibodies or their fragments after selection from phage display libraries", Gene, vol. 187, No. 1, pp. 9-18, 1997.
R&D Systems, "Anti-Human IL-17 Antibody", Ordering Information Sheet, Catalog No. AF-317-NA, Lot No. AB103; Aug. 28, 2007.
Ravetch, J.V., et al., "Structure of the human immunoglobulin .mu. locus: Characterization of embryonic and rearranged J and D genes", Cell, vol. 27, pp. 583-591, 1981.
Riechmann, L., et al., "Reshaping human antibodies for therapy", Nature, vol. 332, pp. 323-324, 1998.
Rouvier, E., et al., "CTLA-8, Clones from an Activated T Cell, Bearing AU-Rich Messenger RNA Instability Sequences, and Homologous to a Herpesvirus Saimiri Gene"., J. Immunol., vol. 150, No. 12, pp. 5445-5456, 1993.
Schier, et al., "Efficient in vitro Affinity Maturation of Phage Antibodies using BIAcore Guided Selections", Human Antibodies and Hybridomas, vol. 7, No. 3, pp. 97-105, 1996.
Schoonjans, et al., "A New Model for Intermediate Molecular Weight Recombinant Bispecific and Trispecific Antibodies by Efficient Heterodimerization of Single Chain Variable Domains Through Fusion to a Fab-Chain", Biomolecular Engineering, vol. 17, No. 6, pp. 193-202, 2001.
Thompson, et al., "Affinity maturation of a high-affinity human monoclonal antibody against the third hypervariable loop of human immunodeficiency virus: use of phage display to improve affinity and broaden strain reactivity", J. Mol. Biol., vol. 256, No. 1, pp. 77-88, 1996.
Thorpe, P.E., et al., The preparation and cytotoxic properties of antibody-toxin conjugates, Immunol. Rev., vol. 62, pp. 119-158, 1982.
Traunecker, A., et al., "Bispecific Single Chain Molecules (Janusins) Target Cytotoxic Lymphocytes on HIV Infected Cells", Embo J., vol. 10, No. 12, pp. 3655-3659, 1991.
Vandamme, et al., "Construction and Characterization of a Recombinant Murine Monoclonal Antibody Directed Against Human Fibrin Fragment-D Dimer", Journal of Biochemistry, vol. 192, pp. 767-775, 1990.
Vaughan, T.J., et al., "Human antibodies by design", Nature Biotechnology, vol. 16, No. 6, pp. 535-539, 1998.
Verma, R., et al., "Antibody engineering: comparison of bacterial, yeast, insect and mammalian expression systems", Journal of Immunological Methods, vol. 216, Nos. 1-2, pp. 165-181, 1998.
Wright, J.F., et al., "The human IL-17F/IL-17A heterodimeric cytokine signals through the IL-17RA/IL-17RC receptor complex", J. Immunol., vol. 181, pp. 2799-2805, 2008.
Wrobel et al. Interleukin-17 in acute myeloid leukemia. J Cell Mol Med. Oct.-Dec. 2003;7(4):472-4.
Yang, W.P., et al., CDR walking mutagenesis for the affinity maturation of a potent human anti-HIV-1 antibody into the picomolar range, J. Mol. Biol., vol. 254, No. 3, pp. 392-403, 1995.

Figure 1

(a) Light Chain variable region of antibody CA028_496 g3 (SEQ ID NO:7)

AIQLTQSPSSLSASVGDRVTITCRADESVRTLMHWYQQKPGKAPKLLIYLVSNSEIGVPDRF
SGSGSGTDFRLTISSLQPEDFATYYCQQTWSDPWTFGQGTKVEIK (b) Heavy Chain variable region of antibody CA028_496 g3 (SEQ ID NO:9)

EVQLVESGGGLVQPGGSLRLSCAASGFTFSDYNMAWVRQAPGKGLEWVATITYEGRNTYYRD
SVKGRFTISRDNAKNSLYLQMNSLRAEDTAVYYCASPPQYYEGSIYRLWFAHWGQGTLVTVS
S (c)

| | |
|---|---|
| CDRH1: | GFTFSDYNMA (SEQ ID NO:1) |
| CDRH2: | TITYEGRNTYYRDSVKG (SEQ ID NO:2) |
| CDRH3: | PPQYYEGSIYRLWFAH (SEQ ID NO:3) |
| CDRL1. | RADESVRTLMH (SEQ ID NO:4) |
| CDRL2: | LVSNSEI (SEQ ID NO:5) |
| CDRL3: | QQTWSDPWT (SEQ ID NO:6) |

(d) Light chain of antibody CA028_496g3 (SEQ ID NO:11)

AIQLTQSPSSLSASVGDRVTITCRADESVRTLMHWYQQKPGKAPKLLIYLVSNSEIGVPDRF
SGSGSGTDFRLTISSLQPEDFATYYCQQTWSDPWTFGQGTKVEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC (e) Light chain of antibody CA028_496g3 including signal (SEQ ID NO:12)

MSVPTQVLGLLLLWLTDARCAIQLTQSPSSLSASVGDRVTITCRADESVRTLMHWYQQKPGK
APKLLIYLVSNSEIGVPDRFSGSGSGTDFRLTISSLQPEDFATYYCQQTWSDPWTFGQGTKV
EIKRTVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC

Figure 2

(a) Heavy chain of antibody CA028_496g3 (SEQ ID NO:15)

EVQLVESGGGLVQPGGSLRLSCAASGFTFSDYNMAWVRQAPGKGLEWVATITYEGRNTYYRD
SVKGRFTISRDNAKNSLYLQMNSLRAEDTAVYYCASPPQYYEGSIYRLWFAHWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGK (b) Heavy chain of antibody CA028_496g3 including signal (SEQ ID NO:16)

MEWSWVFLFFLSVTTGVHSEVQLVESGGGLVQPGGSLRLSCAASGFTFSDYNMAWVRQAPGK
GLEWVATITYEGRNTYYRDSVKGRFTISRDNAKNSLYLQMNSLRAEDTAVYYCASPPQYYEG
SIYRLWFAHWGQGTLVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKKVEPKSCD
KTHTCPPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGK (c) DNA encoding light chain of antibody CA028_496g3 (no signal sequence) (SEQ ID NO:13)

gccatccagctgacccagagcccttcctctctcagcgccagtgtcggagacagagtgactat
tacctgcagggctgacgaaagcgtgagaacattgatgcactggtaccaacagaagcctggca
aagcccccaagctcctgatctatctggtttccaattcggagattggagtccccgacaggttc
agcggcagtgggtctggaactgactttcgcctgacaatctcctcactccagccgaagattt
cgccacctactattgccagcagacttggagcgaccttggacatttggacagggcacaaaag
tggagatcaagcgtacggtagcggccccatctgtcttcatcttcccgccatctgatgagcag
ttgaaatctggaactgcctctgttgtgtgcctgctgaataacttctatcccagagaggccaa
agtacagtggaaggtggataacgccctccaatcgggtaactccaggagagtgtcacagagc
aggacagcaaggacagcacctacagcctcagcagcaccctgacgctgagcaaagcagactac
gagaaacacaaagtctacgcctgcgaagtcacccatcagggcctgagctcgcccgtcacaaa
gagcttcaacaggggagagtgttag

Figure 3

(a) DNA encoding light chain of antibody CA028_496g3 including signal sequence (SEQ ID NO:14)

atgtcagttcccacacaggtgctgggcctgcttctgttgtggctcaccgatgctaggtgtgc
catccagctgacccagagcccttcctctctcagcgccagtgtcggagacagagtgactatta
cctgcagggctgacgaaagcgtgagaacattgatgcactggtaccaacagaagcctggcaaa
gccccaagctcctgatctatctggtttccaattcggagattggagtccccgacaggttcag
cggcagtgggtctggaactgactttcgcctgacaatctcctcactccagcccgaagatttcg
ccacctactattgccagcagacttggagcgaccttggacatttggacagggcacaaaagtg
gagatcaagcgtacggtagcggccccatctgtcttcatcttcccgccatctgatgagcagtt
gaaatctggaactgcctctgttgtgtgcctgctgaataacttctatcccagagaggccaaag
tacagtggaaggtggataacgcctccaatcgggtaactcccaggagagtgtcacagagcag
gacagcaaggacagcacctacagcctcagcagcaccctgacgctgagcaaagcagactacga
gaaacacaaagtctacgcctgcgaagtcacccatcagggcctgagctcgcccgtcacaaaga
gcttcaacaggggagagtgttag (b) DNA encoding Light Chain variable region of antibody CA028_496 g3 (SEQ ID NO:8)

gccatccagctgacccagagcccttcctctctcagcgccagtgtcggagacagagtgactat
tacctgcagggctgacgaaagcgtgagaacattgatgcactggtaccaacagaagcctggca
aagccccaagctcctgatctatctggtttccaattcggagattggagtccccgacaggttc
agcggcagtgggtctggaactgactttcgcctgacaatctcctcactccagcccgaagattt
cgccacctactattgccagcagacttggagcgaccttggacatttggacagggcacaaaag
tggagatcaag (c) DNA encoding Heavy Chain variable region of antibody CA028_496 g3 (SEQ ID NO:10)

gaggttcagctcgttgaatccggaggcggactcgtgcagcctggggctccttgcggctgag
ctgcgctgccagtggcttcactttcagcgattacaatatggcctgggtgcgccaggccccag
gcaagggtctggagtgggtggccacaattacctatgagggcagaaacacttattaccggat
tcagtgaaaggcgatttaccatcagcagggataatgcaaagaacagtctgtacctgcagat
gaactctctgagagctgaggacaccgctgtctactattgtgcaagcccaccccagtactatg
agggctcaatctacagattgtggtttgcccattggggccagggaacactggtgaccgtctcg
agc

Figure 4

DNA (including exons) encoding heavy chain of antibody CA028_496g3 without signal sequence (SEQ ID NO:17)

gaggttcagctcgttgaatccggaggcggactcgtgcagcctgggggctccttgcggctgag
ctgcgctgccagtggcttcactttcagcgattacaatatggcctgggtgcgccaggcccag
gcaagggtctggagtgggtggccacaattacctatgagggcagaaacacttattaccggat
tcagtgaaagggcgatttaccatcagcagggataatgcaaagaacagtctgtacctgcagat
gaactctctgagagctgaggacaccgctgtctactattgtgcaagcccaccccagtactatg
agggctcaatctacagattgtggtttgcccattggggccagggaacactggtgaccgtctcg
agcgcttctacaaagggcccatcggtcttccccctggcaccctcctccaagagcacctctgg
gggcacagcggccctgggctgcctggtcaaggactacttccccgaaccggtgacggtgtcgt
ggaactcaggcgccctgaccagcggcgtgcacaccttcccggctgtcctacagtcctcagga
ctctactccctcagcagcgtggtgaccgtgccctccagcagcttgggcacccagacctacat
ctgcaacgtgaatcacaagcccagcaacaccaaggtcgacaagaaagttgagcccaaatctt
gtgacaaaactcacacatgcccaccgtgcccagcacctgaactcctggggggaccgtcagtc
ttcctcttccccccaaaacccaaggacaccctcatgatctcccggacccctgaggtcacatg
cgtggtggtggacgtgagccacgaagaccctgaggtcaagttcaactggtacgtggacggcg
tggaggtgcataatgccaagacaaagccgcgggaggagcagtacaacagcacgtaccgtgtg
gtcagcgtcctcaccgtcctgcaccaggactggctgaatggcaaggagtacaagtgcaaggt
ctccaacaaagccctcccagccccatcgagaaaaccatctccaaagccaaagcgcagcccc
gagaaccacaggtgtacaccctgccccatcccgggatgagctgaccaagaaccaggtcagc
ctgacctgcctggtcaaaggcttctatcccagcgacatcgccgtggagtgggagagcaatgg
gcagccggagaacaactacaagaccacgcctcccgtgctggactccgacggctccttcttcc
tctacagcaagctcaccgtggacaagagcaggtggcagcaggggaacgtcttctcatgctcc
gtgatgcatgaggctctgcacaaccactacacgcagaagagcctctccctgtctccgggtaa
a Figure 5: DNA encoding heavy chain of antibody CA028_496g3 including signal sequence and exons (SEQ ID NO:18)

atggaatggtcctgggtcttcctgttttccttctgtcacaaccggggtgcacagcgaggt
tcagctcgttgaatccggaggcggactcgtgcagcctgggggctccttgcggctgagctgcg
ctgccagtggcttcactttcagcgattacaatatggcctgggtgcgccaggccccaggcaag
ggtctggagtgggtggccacaattacctatgagggcagaaacacttattacgggattcagt
gaaagggcgatttaccatcagcagggataatgcaaagaacagtctgtacctgcagatgaact
ctctgagagctgaggacaccgctgtctactattgtgcaagcccacccagtactatgagggc
tcaatctacagattgtggtttgcccattggggccagggaacactggtgaccgtctcgagcgc
ttctacaaagggcccatcggtcttcccctggcaccctcctccaagagcacctctggggca
cagcggccctgggctgcctggtcaaggactacttccccgaaccggtgacggtgtcgtggaac
tcaggcgccctgaccagcggcgtgcacaccttcccggctgtcctacagtcctcaggactcta
ctccctcagcagcgtggtgaccgtgcctccagcagcttgggcacccagacctacatctgca
acgtgaatcacaagcccagcaacaccaaggtcgacaagaaagttgagcccaaatcttgtgac
aaaactcacacatgcccaccgtgcccagcacctgaactcctggggggaccgtcagtcttcct
cttccccccaaaacccaaggacaccctcatgatctcccggacccctgaggtcacatgcgtgg
tggtggacgtgagccacgaagaccctgaggtcaagttcaactggtacgtggacggcgtggag
gtgcataatgccaagacaaagccgcgggaggagcagtacaacagcacgtaccgtgtggtcag
cgtcctcaccgtcctgcaccaggactggctgaatggcaaggagtacaagtgcaaggtctcca
acaaagccctcccagcccccatcgagaaaaccatctccaaagccaaagcgcagccccgagaa
ccacaggtgtacaccctgcccccatcccgggatgagctgaccaagaaccaggtcagcctgac
ctgcctggtcaaaggcttctatcccagcgacatcgccgtggagtgggagagcaatgggcagc
cggagaacaactacaagaccacgcctcccgtgctggactccgacggctccttcttcctctac
agcaagctcaccgtggacaagagcaggtggcagcaggggaacgtcttctcatgctccgtgat
gcatgaggctctgcacaaccactacacgcagaagagcctctccctgtctccgggtaaa Figure 6 cDNA encoding heavy chain of antibody CA028_496g3 including signal sequence (SEQ ID NO:19)

atggaatggtcctgggtcttcctgttttcctttctgtcacaaccggggtgcacagcgaggt
tcagctcgttgaatccggaggcggactcgtgcagcctgggggctccttgcggctgagctgcg
ctgccagtggcttcactttcagcgattacaatatggcctgggtgcgccaggcccaggcaag
ggtctggagtgggtggccacaattacctatgagggcagaaacacttattaccgggattcagt
gaaagggcgatttaccatcagcagggataatgcaaagaacagtctgtacctgcagatgaact
ctctgagagctgaggacaccgctgtctactattgtgcaagccacccagtactatgagggc
tcaatctacagattgtggtttgcccattggggccagggaacactggtgaccgtctcgagcgc
ttctacaaagggcccatcggtcttccccctggcaccctcctcaagagcacctctggggca
cagcggccctgggctgcctggtcaaggactacttccccgaaccggtgacggtgtcgtggaac
tcaggcgccctgaccagcggcgtgcacaccttcccggctgtcctacagtcctcaggactcta
ctccctcagcagcgtggtgaccgtgccctccagcagcttgggcacccagacctacatctgca
acgtgaatcacaagcccagcaacaccaaggtcgacaagaaagttgagcccaaatcttgtgac
aaaactcacacatgcccaccgtgcccagcacctgaactcctggggggaccgtcagtcttcct
cttccccccaaaacccaaggacaccctcatgatctcccggacccctgaggtcacatgcgtgg
tggtggacgtgagccacgaagaccctgaggtcaagttcaactggtacgtggacggcgtggag
gtgcataatgccaagacaaagccgcgggaggagcagtacaacagcacgtaccgtgtggtcag
cgtcctcaccgtcctgcaccaggactggctgaatggcaaggagtacaagtgcaaggtctcca
acaaagccctcccagccccatcgagaaaaccatctccaaagccaaagcgcagccccgagaa
ccacaggtgtacaccctgccccatcccgggatgagctgaccaagaaccaggtcagcctgac
ctgcctggtcaaaggcttctatcccagcgacatcgccgtggagtgggagagcaatgggcagc
cggagaacaactacaagaccacgcctcccgtgctggactccgacggctccttcttcctctac
agcaagctcaccgtggacaagagcaggtggcagcaggggaacgtcttctcatgctccgtgat
gcatgaggctctgcacaaccactacacgcagaagagcctctccctgtctccgggtaaa

EXPRESSION VECTOR ENCODING ANTIBODY MOLECULE WHICH BINDS IL-17A AND IL-17F

CROSS-REFERENCE TO RELATED APPLICATIONS

This application is a continuation of U.S. patent application Ser. No. 15/974,407, filed May 8, 2018; which is a continuation of U.S. patent application Ser. No. 14/690,892, filed Apr. 20, 2015; which is a division of U.S. patent application Ser. No. 14/074,880 (now U.S. Pat. No. 9,034,600), filed Nov. 8, 2013; which is a division of U.S. patent application Ser. No. 13/348,456 (now U.S. Pat. No. 8,580,265), filed Jan. 11, 2012; which claims priority to U.S. Provisional Patent Application No. 61/432,814 filed Jan. 14, 2011, which are all incorporated herein by reference in their entireties.

This application contains, as a separate part of disclosure, a Sequence Listing in computer-readable form (filename: 50417D_Seqlisting.txt; Size: 25,440 bytes; created Dec. 15, 2020), which is incorporated by reference in its entirety.

The present invention relates to antibody molecules having specificity for antigenic determinants of both IL-17A and IL-17F. The present invention also relates to the therapeutic uses of the antibody molecules and methods for producing them.

IL-17A (originally named CTLA-8 and also known as IL-17) is a proinflammatory cytokine and the founder member of the IL-17 family (Rouvier et al. 1993, *J. Immunol.* 150: 5445-5456). Subsequently five additional members of the family have been identified (IL-17B-IL-17F) including the most closely related, IL-17F (ML-1) which shares approximately 55% amino acid sequence homology with IL-17A (Moseley et al., 2003, *Cytokine Growth Factor Rev.* 14: 155-174). IL-17A and IL-17F are expressed by the recently defined autoimmune related subset of T helper cells, Th17, that also express IL-21 and IL-22 signature cytokines (Korn et al., 2009, *Annu. Rev. Immunol.* 27:485-517.: 485-517). IL-17A and IL-17F are expressed as homodimers, but may also be expressed as the IL-17A/F heterodimer (Wright et al. 2008, *J. Immunol.* 181: 2799-2805). IL-17A and F signal through the receptors IL-17R, IL-17RC or an IL-17RA/RC receptor complex (Gaffen 2008, *Cytokine.* 43: 402-407). Both IL-17A and IL-17F have been associated with a number of autoimmune diseases.

Accordingly dual antagonists of IL-17A and IL-17F may be more effective than a sole antagonist in treating IL-17 mediated diseases. Antibodies which bind IL-17A and IL-17F have been described in WO2007/106769, WO2008/047134, WO2009/136286 and WO2010/025400.

The present invention provides an improved neutralising antibody which is capable of binding to both IL-17A and IL-17F with high affinity. In particular, the antibody of the present invention is capable of specifically binding to both IL-17A and IL-17F i.e. the antibody does not bind to other isoforms of IL-17. Preferably the antibody of the present invention also binds the IL-17A/IL-17F heterodimer. Preferably, the antibody of the present invention neutralises the activity of both IL-17A and IL-17F. In one embodiment the antibody of the present invention also neutralises the activity of the IL-17A/IL-17F heterodimer. The antibodies of the present invention therefore have the advantageous property that they can inhibit the biological activity of both IL-17A and IL-17F. Accordingly, the present invention also provides the use of such antibodies in the treatment of and/or prophylaxis of a disease mediated by either or both of IL-17A or IL-17F such as autoimmune or inflammatory disease or cancer.

As used herein, the term 'neutralising antibody' describes an antibody that is capable of neutralising the biological signalling activity of both IL-17A and IL17F for example by blocking binding of IL-17A and IL17F to one or more of their receptors and by blocking binding of the IL-17A/IL-17F heterodimer to one or more of its receptors. It will be appreciated that the term 'neutralising' as used herein refers to a reduction in biological signalling activity which may be partial or complete. Further, it will be appreciated that the extent of neutralisation of IL-17A and IL-17F activity by the antibody may be the same or different. In one embodiment the extent of neutralisation of the activity of the IL-17A/IL-17F heterodimer may be the same or different as the extent of neutralisation of IL-17A or IL-17F activity.

In one embodiment the antibodies of the present invention specifically bind to IL-17A and IL-17F. Specifically binding means that the antibodies have a greater affinity for IL-17A and IL-17F polypeptides (including the IL-17A/IL-17F heterodimer) than for other polypeptides. Preferably the IL-17A and IL-17F polypeptides are human. In one embodiment the antibody also binds cynomolgus IL-17A and IL-17F.

IL-17A or IL-17F polypeptides or a mixture of the two or cells expressing one or both of said polypeptides can be used to produce antibodies which specifically recognise both polypeptides. The IL-17 polypeptides (IL-17A and IL-17F) may be 'mature' polypeptides or biologically active fragments or derivatives thereof which preferably include the receptor binding site. Preferably the IL-17 polypeptides are the mature polypeptides. IL-17 polypeptides may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The IL-17 polypeptide may in some instances be part of a larger protein such as a fusion protein for example fused to an affinity tag. Antibodies generated against these polypeptides may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows or pigs may be immunized. However, mice, rabbits, pigs and rats are generally preferred.

Antibodies for use in the present invention include whole antibodies and functionally active fragments or derivatives thereof and may be, but are not limited to, monoclonal, multi-valent, multi-specific, bispecific, humanized or chimeric antibodies, domain antibodies e.g. VH, VL, VHH, single chain antibodies, Fv, Fab fragments, Fab' and F(ab')$_2$ fragments and epitope-binding fragments of any of the above. Other antibody fragments include those described in International patent applications WO2005003169, WO2005003170 and WO2005003171. Other antibody fragments include Fab-Fv and Fab-dsFv fragments described in WO2009040562 and WO2010035012 respectively. Antibody fragments and methods of producing them are well known in the art, see for example Verma et al., 1998, Journal of Immunological Methods, 216, 165-181; Adair and Lawson, 2005. Therapeutic antibodies. *Drug Design Reviews—Online* 2(3):209-217.

Antibodies for use in the present invention include immunoglobulin molecules and immunologically active portions of immunoglobulin molecules, i.e. molecules that contain an antigen binding site that specifically binds an antigen. The immunoglobulin molecules of the invention can be of any class (e.g. IgG, IgE, IgM, IgD and IgA) or subclass of immunoglobulin molecule.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp. 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93(15): 7843-78481; WO92/02551; WO2004/051268 and International Patent Application number WO2004/106377.

Humanized antibodies are antibody molecules from non-human species having one or more complementarity determining regions (CDRs) from the non-human species and a framework region from a human immunoglobulin molecule (see, e.g. U.S. Pat. No. 5,585,089; WO91/09967).

Chimeric antibodies are those antibodies encoded by immunoglobulin genes that have been genetically engineered so that the light and heavy chain genes are composed of immunoglobulin gene segments belonging to different species. These chimeric antibodies are likely to be less antigenic.

Bivalent antibodies may be made by methods known in the art (Milstein et al., 1983, Nature 305:537-539; WO 93/08829, Traunecker et al., 1991, EMBO J. 10:3655-3659). Multi-valent antibodies may comprise multiple specificities or may be monospecific (see for example WO 92/22853 and WO05/113605).

The antibodies for use in the present invention can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108. Techniques for the production of single chain antibodies, such as those described in U.S. Pat. No. 4,946,778 can also be adapted to produce single chain antibodies which bind to IL-17A and IL-17F. Also, transgenic mice, or other organisms, including other mammals, may be used to express humanized antibodies.

Screening for antibodies can be performed using assays to measure binding to human IL-17A and human IL-17F, for example BIAcore™ assays described in the Examples herein. Suitable neutralisation assays are known in the art, see for example WO2008/047134 and the Examples herein.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus 'CDR-H1', as used herein, comprises residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

In one embodiment the present invention provides a neutralising antibody having specificity for human IL-17A and human IL-17F, comprising a light chain, wherein the variable domain of the light chain comprises the sequence given in SEQ ID NO:4 for CDR-L1, the sequence given in SEQ ID NO:5 for CDR-L2 and the sequence given in SEQ ID NO:6 for CDR-L3 (See FIG. 1c).

The antibody molecules of the present invention preferably comprise a complementary heavy chain.

Accordingly, in one embodiment the present invention provides a neutralising antibody having specificity for human IL-17A and human IL-17F, further comprising a heavy chain, wherein the variable domain of the heavy chain comprises at least one of a CDR having the sequence given in SEQ ID NO:1 for CDR-H1, a CDR having the sequence given in SEQ ID NO:2 for CDR-H2 and a CDR having the sequence given in SEQ ID NO:3 for CDR-H3 (See FIG. 1c).

In another embodiment the present invention provides a neutralising antibody having specificity for human IL-17A and human IL-17F, comprising a heavy chain, wherein at least two of CDR-H1, CDR-H2 and CDR-H3 of the variable domain of the heavy chain are selected from the following: the sequence given in SEQ ID NO:1 for CDR-H1, the sequence given in SEQ ID NO:2 for CDR-H2 and the sequence given in SEQ ID NO:3 for CDR-H3. For example, the antibody may comprise a heavy chain wherein CDR-H1 has the sequence given in SEQ ID NO:1 and CDR-H2 has the sequence given in SEQ ID NO:2. Alternatively, the antibody may comprise a heavy chain wherein CDR-H1 has the sequence given in SEQ ID NO:1 and CDR-H3 has the sequence given in SEQ ID NO:3, or the antibody may comprise a heavy chain wherein CDR-H2 has the sequence given in SEQ ID NO:2 and CDR-H3 has the sequence given in SEQ ID NO:3. For the avoidance of doubt, it is understood that all permutations are included.

In another embodiment the present invention provides a neutralising antibody having specificity for human IL-17A and human IL-17F, comprising a heavy chain, wherein the variable domain of the heavy chain comprises the sequence given in SEQ ID NO:1 for CDR-H1, the sequence given in SEQ ID NO:2 for CDR-H2 and the sequence given in SEQ ID NO:3 for CDR-H3.

In one embodiment, an antibody according to the present invention comprises a heavy chain, wherein the variable domain of the heavy chain comprises the sequence given in SEQ ID NO:1 for CDR-H1, the sequence given in SEQ ID NO:2 for CDR-H2 and the sequence given in SEQ ID NO:3 for CDR-H3 and a light chain wherein the variable domain of the light chain comprises the sequence given in SEQ ID NO:4 for CDR-L1, the sequence given in SEQ ID NO:5 for CDR-L2 and the sequence given in SEQ ID NO:6 for CDR-L3.

In one embodiment the antibody provided by the present invention is a monoclonal antibody.

In one embodiment the antibody provided by the present invention is a CDR-grafted antibody molecule comprising each of the CDRs provided in SEQ ID NOS:1 to 6. As used herein, the term 'CDR-grafted antibody molecule' refers to an antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, *Methods*, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Preferably, the CDR-grafted antibody according to the present invention has a variable domain comprising human acceptor framework regions as well as one or more of the CDRs or specificity determining residues described above. Thus, provided in one embodiment is a neutralising CDR-grafted antibody wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: http://vbase.mrc-cpe.cam.ac.uk/

In a CDR-grafted antibody of the present invention, the acceptor heavy and light chains do not necessarily need to be derived from the same antibody and may, if desired, comprise composite chains having framework regions derived from different chains.

The preferred framework region for the heavy chain of the CDR-grafted antibody of the present invention is derived from the human sub-group VH3 sequence 1-3 3-07 together with JH4, as previously described in WO2008/047134. Accordingly, provided is a neutralising CDR-grafted antibody comprising at least one non-human donor CDR wherein the heavy chain framework region is derived from the human subgroup sequence 1-3 3-07 together with JH4. The sequence of human JH4 is as follows: (YFDY) WGQGTLVTVSS. The YFDY motif is part of CDR-H3 and is not part of framework 4 (Ravetch, J V. et al., 1981, *Cell*, 27, 583-591).

The preferred framework region for the light chain of the CDR-grafted antibody of the present invention is derived from the human germline sub-group VK1 sequence 2-1-(1) L4 together with JK1, as previously described in WO2008/047134. Accordingly, provided is a neutralising CDR-grafted antibody comprising at least one non-human donor CDR wherein the light chain framework region is derived from the human subgroup sequence VK1 2-1-(1) L4 together with JK1. The JK1 sequence is as follows: (WT) FGQGTKVEIK. The WT motif is part of CDR-L3 and is not part of framework 4 (Hieter, P A., et al., 1982, J. Biol. Chem., 257, 1516-1522).

Also, in a CDR-grafted antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

Preferably, in a CDR-grafted antibody molecule of the present invention, if the acceptor heavy chain has the human VH3 sequence 1-3 3-07 together with JH4, then the acceptor framework regions of the heavy chain comprise, in addition to one or more donor CDRs, a donor residue at at least position 94 (according to Kabat et al., (supra)). Accordingly, provided is a CDR-grafted antibody, wherein at least the residue at position 94 of the variable domain of the heavy chain is a donor residue.

Preferably, in a CDR-grafted antibody molecule according to the present invention, if the acceptor light chain has the human sub-group VK1 2-1-(1) L4 together with JK1, then no donor residues are transferred i.e. only the CDRs are transferred. Accordingly, provided is a CDR-grafted antibody wherein only the CDRs are transferred to the donor framework.

Donor residues are residues from the donor antibody, i.e. the antibody from which the CDRs were originally derived.

In the present invention the antibody known as CA028_0496 (previously described in WO2008/047134) was improved by changing five residues in the light chain. Three residues were in the CDRs and two in the framework. Accordingly in one embodiment the light chain variable domain comprises an arginine residue at position 30, a serine residue at position 54, an isoleucine residue at position 56, an aspartic acid residue at position 60 and an arginine residue at position 72.

Accordingly, in one embodiment, an antibody of the present invention comprises a light chain, wherein the variable domain of the light chain comprises the sequence given in SEQ ID NO:7 (gL7).

In another embodiment, an antibody of the present invention comprises a light chain, wherein the variable domain of the light chain comprises a sequence having at least 96% identity to the sequence given in SEQ ID NO:7. In one embodiment the antibody of the present invention comprises a light chain, wherein the variable domain of the light chain comprises a sequence having at least 97, 98 or 99% identity to the sequence given in SEQ ID NO:7.

In one embodiment, an antibody of the present invention comprises a heavy chain, wherein the variable domain of the heavy chain comprises the sequence given in SEQ ID NO:9 (gH9).

In another embodiment, an antibody of the present invention comprises a heavy chain, wherein the variable domain of the heavy chain comprises a sequence having at least 60% identity or similarity to the sequence given in SEQ ID NO:9. In one embodiment, an antibody of the present invention comprises a heavy chain, wherein the variable domain of the heavy chain comprises a sequence having at least 70%, 80%, 90%, 95%, 96, 97, 98 or 99% identity or similarity to the sequence given in SEQ ID NO:9.

In one embodiment an antibody of the present invention comprises a heavy chain, wherein the variable domain of the heavy chain comprises the sequence given in SEQ ID NO:9 and a light chain, wherein the variable domain of the light chain comprises the sequence given in SEQ ID NO:7.

In another embodiment of the invention, the antibody comprises a heavy chain and a light chain, wherein the variable domain of the heavy chain comprises a sequence having at least 60% identity or similarity to the sequence given in SEQ ID NO:9 and the variable domain of the light chain comprises a sequence having at least 96% identity to the sequence given in SEQ ID NO:7. Preferably, the antibody comprises a heavy chain, wherein the variable domain of the heavy chain comprises a sequence having at least 70%, 80%, 90%, 95%, 96%, 97%, 98 or 99% identity or similarity to the sequence given in SEQ ID NO:9 and a light chain, wherein the variable domain of the light chain comprises a sequence having at least 96, 97, 98 or 99% identity to the sequence given in SEQ ID NO:7.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:
  phenylalanine, tyrosine and tryptophan (amino acids having aromatic side chains);
  lysine, arginine and histidine (amino acids having basic side chains);
  aspartate and glutamate (amino acids having acidic side chains);
  asparagine and glutamine (amino acids having amide side chains); and
  cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

The antibody molecule of the present invention may comprise a complete antibody molecule having full length heavy and light chains or a fragment thereof, such as a domain antibody e.g. VH, VL, VHH, Fab, modified Fab, Fab', F(ab')2, Fv or scFv fragment. Other antibody fragments include Fab-Fv and Fab-dsFv fragments described in WO2009040562 and WO2010035012 respectively. In one embodiment the antibody fragment of the present invention is selected from the group consisting of a Fab, Fab', F(ab')2, scFv and Fv fragment.

It will be appreciated that the antibodies of the present invention, in particular the antibody fragments described above, may be incorporated into other antibody formats, in particular, multi-specific antibodies, such as bi or tri specific antibodies, where one specificity is provided by an antibody of the present invention i.e specificity for IL-17A and IL-17F (including IL-17A/F heterodimer). Accordingly, in one embodiment the present invention provides a multi-specific antibody comprising one or more of the antibody fragments described herein above.

Examples of multi-specific antibodies include bi, tri or tetra-valent antibodies, Bis-scFv, diabodies, triabodies, tetrabodies, bibodies and tribodies (see for example Holliger and Hudson, 2005, Nature Biotech 23(9): 1126-1136; Schoonjans et al. 2001, Biomolecular Engineering, 17 (6), 193-202). Other multi-specific antibodies include Fab-Fv, Fab-dsFv, Fab-Fv-Fv. Fab-Fv-Fc and Fab-dsFv-PEG fragments described in WO2009040562, WO2010035012, WO2011/08609, WO2011/030107 and WO2011/061492 respectively.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply blocking IL-17 activity. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. Particularly preferred is the IgG1 constant domain. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705:129-134, 1995). Accordingly, the C-terminal lysine of the antibody heavy chain, for example as given in FIG. 2 (*a*), SEQ ID NO: 15, may be absent.

In one embodiment the antibody heavy chain comprises a CH1 domain and the antibody light chain comprises a CL domain, either kappa or lambda.

In a preferred embodiment the antibody provided by the present invention is a neutralising antibody having specificity for human IL-17A and human IL-17F in which the heavy chain constant region comprises the human IgG1 constant region. Accordingly, the present invention provides an antibody in which the heavy chain comprises or consists of the sequence given in SEQ ID NO:15 (See FIG. 2a).

In one embodiment of the invention, the antibody comprises a heavy chain, wherein the heavy chain comprises a sequence having at least 60% identity or similarity to the sequence given in SEQ ID NO:15. Preferably, the antibody comprises a heavy chain, wherein the heavy chain comprises a sequence having at least 70%, 80%, 90%, 95%, 96%, 97%, 98% or 99% identity or similarity to the sequence given in SEQ ID NO:15

In one embodiment an antibody molecule according to the present invention comprises a light chain comprising the sequence given in SEQ ID NO:11 (See FIG. 1d).

In one embodiment of the invention, the antibody comprises a light chain, wherein the light chain comprises a sequence having at least 60% identity or similarity to the sequence given in SEQ ID NO:11. Preferably, the antibody comprises a light chain, wherein the light chain comprises a sequence having at least 70%, 80%, 90%, 95% or 98% identity or similarity to the sequence given in SEQ ID NO:11.

In one embodiment the present invention provides an antibody in which the heavy chain comprises or consists of the sequence given in SEQ ID NO:15 and the light chain comprises or consists of the sequence given in SEQ ID NO:11.

In one embodiment of the invention, the antibody comprises a heavy chain and a light chain, wherein the heavy chain comprises a sequence having at least 60% identity or similarity to the sequence given in SEQ ID NO:15 and the light chain comprises a sequence having at least 60% identity or similarity to the sequence given in SEQ ID NO:11. Preferably, the antibody comprises a heavy chain, wherein the heavy chain comprises a sequence having at least 70%, 80%, 90%, 95% or 98% identity or similarity to the sequence given in SEQ ID NO:15 and a light chain, wherein the light chain comprises a sequence having at least 70%, 80%, 90%, 95% or 98% identity or similarity to the sequence given in SEQ ID NO:11.

The antibody molecule of any aspect of the present invention preferably has a high binding affinity, preferably picomolar. It will be appreciated that the binding affinity of an antibody according to the present invention for human IL-17A may be different from the binding affinity of the same antibody for human IL-17F and/or the IL-17A/F heterodimer. In one example the antibody molecule of the present invention has an affinity for IL-17A that is greater than its affinity for IL-17F. In one example the antibody molecule of the present invention has an affinity for IL-17A which is at least 5 fold greater than its binding affinity for IL-17F. In one example the antibody molecule of the present invention has an affinity for IL-17A that is the same as its affinity for IL-17F. In one example the antibody molecule of the present invention has a picomolar affinity for both IL-17A and IL-17F.

Affinity may be measured using any suitable method known in the art, including BIAcore™, as described in the Examples herein, using isolated natural or recombinant IL-17A and IL-17F which both exist as homodimers.

Preferably the antibody molecule of the present invention has a binding affinity for IL-17A of 50 pM or less. In one embodiment the antibody molecule of the present invention has a binding affinity for IL-17A of 20 pM or less. In one embodiment the antibody molecule of the present invention has a binding affinity for IL-17A of 10 pM or less. In one embodiment the antibody molecule of the present invention has a binding affinity for IL-17A of 5 pM or less. In one embodiment the antibody of the present invention has an affinity for IL-17A of 3.2 pM.

Preferably the antibody molecule of the present invention has a binding affinity for IL-17F of 100 pM or less. In one embodiment the antibody of the present invention has an affinity for IL-17F of 50 pM or less. In one embodiment the antibody of the present invention has an affinity for IL-17F of 23 pM.

It will be appreciated that the affinity of antibodies provided by the present invention may be altered using any suitable method known in the art. The present invention therefore also relates to variants of the antibody molecules of the present invention, which have an improved affinity for IL-17A and/or IL-17F. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

If desired an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO03081581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, *Pseudomonas* exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

In one embodiment, the present invention provides a neutralising antibody molecule having specificity for human IL-17A and human IL-17F, which is a modified Fab fragment having a heavy chain comprising the sequence given in SEQ ID NO:9 and a light chain comprising the sequence given in SEQ ID NO:7 and having at the C-terminal end of its heavy chain a modified hinge region containing at least one cysteine residue to which an effector molecule is attached. Preferably the effector molecule is PEG and is attached using the methods described in (WO98/25971 and WO2004072116) whereby a lysyl-maleimide group is attached to the cysteine residue at the C-terminal end of the heavy chain, and each amino group of the lysyl residue has covalently linked to it a methoxypoly(ethyleneglycol) residue having a molecular weight of about 20,000 Da. The total molecular weight of the PEG attached to the antibody is therefore approximately 40,000 Da.

In another example effector molecules may be attached to antibody fragments using the methods described in International patent applications WO2005/003169, WO2005/003170 and WO2005/003171.

The present invention also provides an isolated DNA sequence encoding the heavy and/or light chain(s) of an antibody molecule of the present invention. Preferably, the DNA sequence encodes the heavy or the light chain of an antibody molecule of the present invention. The DNA sequence of the present invention may comprise synthetic DNA, for instance produced by chemical processing, cDNA, genomic DNA or any combination thereof.

DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Examples of suitable sequences are provided in SEQ ID NO:8; SEQ ID NO:10; SEQ ID NO:13; SEQ ID NO:14; SEQ ID NO:17, SEQ ID NO:18 and SEQ ID NO:19.

The present invention also relates to a cloning or expression vector comprising one or more DNA sequences of the present invention. Accordingly, provided is a cloning or expression vector comprising one or more DNA sequences encoding an antibody of the present invention. Preferably, the cloning or expression vector comprises two DNA sequences, encoding the light chain and the heavy chain of the antibody molecule of the present invention, respectively along with suitable signal sequences. Preferably, a vector according to the present invention comprises the sequences given in SEQ ID NO:14 and SEQ ID NO:18. In one embodiment a vector according to the present invention comprises the sequences given in SEQ ID NO:13 and SEQ ID NO:17.

General methods by which the vectors may be constructed, transfection methods and culture methods are well known to those skilled in the art. In this respect, reference is made to "Current Protocols in Molecular Biology", 1999, F.

M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example E. coli, and other microbial systems may be used or eukaryotic, for example mammalian, host cell expression systems may also be used. Suitable mammalian host cells include CHO, myeloma or hybridoma cells.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

As the antibodies of the present invention are useful in the treatment and/or prophylaxis of a pathological condition, the present invention also provides a pharmaceutical or diagnostic composition comprising an antibody molecule of the present invention in combination with one or more of a pharmaceutically acceptable excipient, diluent or carrier. Accordingly, provided is the use of an antibody according to the present invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody molecule of the present invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines or a small molecule inhibitor.

The pharmaceutical compositions preferably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, preferably 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which the antibody molecule of the present invention is administered depends on the nature of the condition to be treated, the extent of the inflammation present and on whether the antibody molecule is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Preferred forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO 98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 μm, in particular from 1 to 5 μm. The particle size of the active ingredient (such as the antibody or fragment) is of primary importance.

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The antibody of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the antibody in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 mL, of solvent/solution buffer.

The antibodies disclosed herein may be suitable for delivery via nebulisation.

It is also envisaged that the antibody of the present invention may be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The present invention also provides an antibody molecule for use in the control of inflammatory diseases. Preferably, the antibody molecule can be used to reduce the inflammatory process or to prevent the inflammatory process.

The present invention also provides the antibody molecule of the present invention for use in the treatment or prophylaxis of a pathological disorder that is mediated by IL-17A and/or IL-17F or is associated with an increased level of IL-17A and/or IL-17F. Preferably, the pathological condition is selected from the group consisting of infections (viral, bacterial, fungal and parasitic), endotoxic shock associated with infection, arthritis, rheumatoid arthritis, psoriatic arthritis, systemic onset juvenile idiopathic arthritis (JIA), systemic lupus erythematosus (SLE), asthma, chronic obstructive airways disease (COAD), chronic obstructive pulmonary disease (COPD), acute lung injury, pelvic inflammatory disease, Alzheimer's Disease, Crohn's disease, inflammatory bowel disease, irritable bwel syndrome, Ulcerative colitis, Castleman's disease, ankylosing spondylitis and other spondyloarthropathies, dermatomyositis, myocarditis, uveitis, exophthalmos, autoimmune thyroiditis, Peyronie's Disease, coeliac disease, gallbladder disease, Pilonidal disease, peritonitis, psoriasis, atopic dermatitis, vasculitis, surgical adhesions, stroke, autoimmune diabetes, Type I Diabetes, lyme arthritis, meningoencephalitis, immune mediated inflammatory disorders of the central and peripheral nervous system such as multiple sclerosis and Guillain-Barr syndrome, other autoimmune disorders, pancreatitis, trauma (surgery), graft-versus-host disease, transplant rejection, fibrosing disorders including pulmonary fibrosis, liver fibrosis, renal fibrosis, scleroderma or systemic sclerosis, cancer (both solid tumours such as melanomas, hepatoblastomas, sarcomas, squamous cell carcinomas, transitional cell cancers, ovarian cancers and hematologic malignancies and in particular acute myelogenous leukaemia, chronic myelogenous leukemia, chronic lymphatic leukemia, gastric cancer and colon cancer), heart disease including ischaemic diseases such as myocardial infarction as well as atherosclerosis, intravascular coagulation, bone resorption, osteoporosis, periodontitis and hypochlorhydia.

In one embodiment the antibody of the present invention is used in the treatment or prophylaxis of a pathological disorder selected from the group consisting of arthritis, rheumatoid arthritis, psoriasis, psoriatic arthritis, systemic onset juvenile idiopathic arthritis (JIA), systemic lupus erythematosus (SLE), asthma, chronic obstructive airway disease, chronic obstructive pulmonary disease, atopic dermatitis, scleroderma, systemic sclerosis, lung fibrosis, inflammatory bowel diseases, ankylosing spondylitis and other spondyloarthropathies and cancer.

In one embodiment the antibody of the present invention is used in the treatment or prophylaxis of a pathological disorder selected from the group consisting of arthritis, rheumatoid arthritis, psoriasis, psoriatic arthritis, systemic onset juvenile idiopathic arthritis (JIA), systemic lupus erythematosus (SLE), asthma, chronic obstructive airway disease, chronic obstructive pulmonary disease, atopic dermatitis, scleroderma, systemic sclerosis, lung fibrosis, Crohn's disease, ulcerative colitis, ankylosing spondylitis and other spondyloarthropathies and cancer.

In one embodiment the antibody of the present invention is used in the treatment or prophylaxis of a pathological disorder selected from the group consisting of arthritis, rheumatoid arthritis, psoriasis, psoriatic arthritis, systemic onset juvenile idiopathic arthritis (JIA), systemic lupus erythematosus (SLE), asthma, chronic obstructive airway disease, chronic obstructive pulmonary disease, atopic dermatitis, scleroderma, systemic sclerosis, lung fibrosis, Crohn's disease, ulcerative colitis, ankylosing spondylitis and other spondyloarthropathies.

In one embodiment the pathological disorder is rheumatoid arthritis.

In one embodiment the pathological disorder is Crohn's disease.

In one embodiment the pathological disorder is ulcerative colitis.

In one example the antibody of the present invention is used in the treatment of an inflammatory or immune related disease. In one example the inflammatory or immune related disease is selected from the group consisting of rheumatoid arthritis, Crohn's disease and ulcerative colitis.

The present invention also provides an antibody molecule according to the present invention for use in the treatment or prophylaxis of pain, particularly pain associated with inflammation.

The present invention further provides the use of an antibody molecule according to the present invention in the manufacture of a medicament for the treatment or prophylaxis of a pathological disorder that is mediated by IL-17A and/or IL-17F or associated with an increased level of IL-17A and/or IL-17F. Preferably the pathological disorder is one of the medical indications described herein above. The present invention further provides the use of an antibody molecule according to the present invention in the manufacture of a medicament for the treatment or prophylaxis of pain, particularly pain associated with inflammation.

An antibody molecule of the present invention may be utilised in any therapy where it is desired to reduce the effects of IL-17A and/or IL-17F in the human or animal body. IL-17 A and/or IL-17F may be circulating in the body or may be present in an undesirably high level localised at a particular site in the body, for example a site of inflammation.

An antibody molecule according to the present invention is preferably used for the control of inflammatory disease, autoimmune disease or cancer.

The present invention also provides a method of treating human or animal subjects suffering from or at risk of a disorder mediated by IL-17A and/or IL-17F, the method comprising administering to the subject an effective amount of an antibody molecule of the present invention.

An antibody molecule according to the present invention may also be used in diagnosis, for example in the in vivo diagnosis and imaging of disease states involving IL-17A and/or IL-17F.

The present invention is further described by way of illustration only in the following examples, which refer to the accompanying Figures, in which:

FIG. 1
a) Light chain V region of antibody CA028_0496 g3 (SEQ ID NO:7)
b) Heavy chain V region of antibody CA028_0496 g3 (SEQ ID NO:9)
c) CDRH1 (SEQ ID NO:1), CDRH2 (SEQ ID NO:2), CDRH3 (SEQ ID NO:3), CDRL1 (SEQ ID NO:4), CDRL2 (SEQ ID NO:5), CDRL3 (SEQ ID NO:6) of antibody CA028_496 g3.
d) Light chain of antibody CA028_496 g3 (SEQ ID NO:11).
e) Light chain of antibody CA028_496 g3 including signal sequence (SEQ ID NO:12).

FIG. 2
a) Heavy chain of antibody CA028_496 g3 (SEQ ID NO:15).
b) Heavy chain of antibody CA028_496 g3 including signal sequence (SEQ ID NO:16).
c) DNA encoding light chain of antibody CA028_496 g3 (no signal sequence) (SEQ ID NO:13).

FIG. 3
a) DNA encoding light chain of antibody CA028_496 g3 including signal sequence (SEQ ID NO:14)
b) DNA encoding light chain variable region of antibody CA028_496 g3 (SEQ ID NO:8)

c) DNA encoding heavy chain variable region of antibody CA028_496 g3 including signal sequence (SEQ ID NO:10)

FIG. 4: DNA (including exons) encoding heavy chain of antibody CA028_496 g3 without signal sequence (SEQ ID NO:17)

FIG. 5: DNA (including exons and signal sequence) encoding heavy chain of antibody CA028_496 g3 (SEQ ID NO:18)

FIG. 6: c DNA encoding heavy chain of antibody CA028_496 g3 including signal sequence (SEQ ID NO:19).

FIG. 7: The effect of antibodies CA028_0496 (designated 496g1 in legend) and CA028_00496. g3 (designated 496.g3 in legend) on human IL-17F induced IL-6 production from Hela cells.

EXAMPLE 1: PRODUCTION OF AN IMPROVED NEUTRALISING ANTIBODY WHICH BINDS IL-17A AND IL-17F

The isolation and humanisation of antibody CA028_0496 has previously been described in WO2008/047134. CA028_0496 is a humanised neutralising antibody which binds both IL-17A and IL-17F and comprises the grafted variable regions gL7 and gH9, the sequences of which are provided in WO2008/047134. The heavy chain acceptor framework is the human germline sequence VH3 1-3 3-07 with framework 4 coming from this portion of the human JH-region germline JH4. The light chain acceptor framework is the human germline sequence VK1 2-1-(1) L4, with framework 4 coming from this portion of the human JK-region germline JK1.

Antibody CA028_00496 was affinity matured to improve the affinity of the antibody for IL-17F whilst retaining affinity for IL-17A. In contrast to antibody CA028_00496, the affinity matured antibody, known as CA028_00496. g3, was expressed as an IgG1 rather than an IgG4. Genes were modified to generate the affinity matured versions by oligonucleotide directed mutagenesis. The affinity matured light chain variable region (gL57) gene sequence was sub-cloned into the UCB Celltech human light chain expression vector pKH10.1, which contains DNA encoding the human C-Kappa constant region (Km3 allotype). The unaltered heavy chain variable region (gH9) sequence was sub-cloned into the UCB Celltech expression vector pVhg 1 FL, which contains DNA encoding human heavy chain gamma-1 constant regions. Plasmids were co-transfected into CHO cells using the Lipofectamine™ 2000 procedure according to manufacturer's instructions (InVitrogen, catalogue No. 11668).

The final sequence of the affinity matured variable regions of antibody CA028_00496. g3 are given in FIGS. 1a and 1b. In antibody CA028_00496. g3 the heavy chain variable region sequence is the same as that of the parent antibody CA028_00496. In contrast, the light chain variable region differs by 5 amino acids. The five residues that differ between the light chain of antibody CA028_00496 and antibody CA028_00496. g3 are underlined in FIG. 1a.

EXAMPLE 2: BIACORE

As described below, the assay format was capture of the antibody CA028_00496. g3 by an immobilised anti-human IgG Fc-specific antibody, followed by titration of human IL-17A and human IL-17F over the captured surface.

Biamolecular Interaction Analysis was performed using a Biacore 3000 (Biacore AB). Assays were performed at 25° C. Affinipure F(ab')$_2$ fragment goat anti-human IgG Fc specific (Jackson ImmunoResearch) was immobilised on a CM5 Sensor Chip (Biacore AB) via amine coupling chemistry to a level of approximately 6000 response units (RU). HBS-EP buffer (10 mM HEPES pH7.4, 0.15M NaCl, 3 mM EDTA, 0.005% Surfactant P20, Biacore AB) was used as the running buffer with a flow rate of 10 µL/minute (min). A 10 µL injection of CA028_00496. g3 at 0.5 µg/mL was used for capture by the immobilised anti-human IgG Fc. Human IL-17A (generated in house by UCB) was titrated over the captured CA028_00496. g3 from 5 nM at a flow rate of 30 µL/min for 3 min followed by a 20 min dissociation. Human IL-17F (R&D systems) was titrated over the captured CA028_00496. g3 from 10 nM at a flow rate of 30 µL/min for 3 min followed by a 5 min dissociation. The surface was regenerated at a flow rate of 10 µL/min by a 10 µL injection of 40 mM HCl followed by a 5 µL injection of 5 mM NaOH.

TABLE 1

| Affinity of CA028_496.g3 against human IL-17F and IL-17A | | | | |
|---|---|---|---|---|
| | $k_a$ (M$^{-1}$s$^{-1}$) | $k_d$ (s$^{-1}$) | $K_D$ (M) | KD (pM) |
| hIL-17F | 2.49E+06 | 8.74E−05 | 3.51E−11 | 35 |
| | 3.49E+06 | 5.08E−05 | 1.46E−11 | 15 |
| | 2.99E+06 | 6.91E−05 | 2.31E−11 | 23 |
| hIL-17A | 4.66E+06 | 2.04E−05 | 4.38E−12 | 4.4 |
| | 4.52E+06 | 8.66E−06 | 1.92E−12 | 1.9 |
| | 4.59E+06 | 1.45E−05 | 3.17E−12 | 3.2 |

Double referenced background subtracted binding curves were analysed using the BIAevaluation software (version 4.1) following standard procedures. Kinetic parameters were determined from the fitting algorithm. Data are detailed in Table 1, average values are highlighted in grey.

The affinity value determined for the original antibody CA028_0496 binding IL-17A was 16 pM and 1750 pM for IL-17F. In contrast, the improved antibody CA028_0496 g3 has an affinity for IL-17A of 3.2 pM and for IL-17F of 23 pM. The affinity of antibody CA028_0496 for IL-17F was improved over 70 fold without reducing the affinity of the antibody for IL-17A. Infact, affinity for IL-17A was increased five fold.

The affinity of CA028_0496 g3 was also improved for IL-17A/F heterodimer (made as described in WO2008/047134) where affinity was found to be 26 pM (data not shown).

EXAMPLE 3

The potency of CA028_00496.g1 (previously described in WO2008/047134) and CA028_00496.g3 for the neutralisation of human IL-17F was determined using a HeLa cell bioassay. Hela cells were obtained from the cell bank at ATCC (ATCC CCL-2). Cells were grown in Dulbecco's modified Eagle's medium (DMEM) supplemented with 10% foetal calf serum, penicillin, gentamycin and glutamine. 1×10$^4$ cells were plated out into 96 well flat bottomed tissue culture plates. Cells were incubated overnight and washed once in assay buffer. HeLa cells were stimulated with a combination of recombinant human IL-17F (125 ng/ml) and tumour necrosis factor-alpha (TNF-α) (1 ng/ml) for 48 hours in the presence of varying concentrations of the antibodies. In the HeLa cell line, IL-17F synergises with TNF-alpha to induce the production of IL-6 which can be quantified using a specific MSD assay kit. The resulting amount of secreted IL-6 was measured using Meso Scale Discovery (MSD)

assay technology and IC50 values calculated. CA028_00496.g1 and CA028_00496.g3 showed dose-dependent inhibition of the bioactivity of IL-17F as measured in the HeLa cell bioassay (FIG. 7). The activity of CA028_00496.g1 and CA028_00496.g3 in the HeLa assay was expressed as the dose required to inhibit 50% of the activity of IL-17F ($IC_{50}$). The $IC_{50}$ for CA028_00496.g1 is 92 mg/mL and for CAO 496.g3 is 4 ng/mL.

The ability of CA028_00496.g3 to neutralise IL-17A, as described previously for CA028_00496.g1 in WO2008/047134, was confirmed using the same assay in which IL-17F was replaced with IL-17A (data not shown).

The complete content of all publications, patents and patent applications cited herein are hereby in their entireties.

The foregoing invention has been described by way of illustration and example. The above examples are provided for exemplification purposes only and are not intended to limit the scope of the invention. It will be readily apparent to one skilled in the art in light of the teachings of this invention that changes and modifications can be made without departing from the spirit and scope of the present invention.

What is claimed is:

1. An expression vector comprising the nucleic acid sequence set forth in SEQ ID NO: 14.

2. The expression vector of claim 1, further comprising the nucleic acid sequence set forth in SEQ ID NO: 10.

3. A host cell comprising the expression vector of claim 1.

4. A method comprising culturing the host cell of claim 3 under conditions suitable for the expression of the nucleic acid.

5. The host cell of claim 3, wherein the expression vector further comprises the nucleic acid sequence set forth in SEQ ID NO: 10.

6. A method comprising culturing the host cell of claim 5 under conditions suitable for the expression of the nucleic acids.

7. The host cell of claim 3, further comprising an expression vector comprising the nucleic acid sequence set forth in SEQ ID NO: 10.

8. A method comprising culturing the host cell of claim 7 under conditions suitable for the expression of the nucleic acids.

* * * * *

SEQUENCE LISTING

```
<160> NUMBER OF SEQ ID NOS: 19

<210> SEQ ID NO 1
<211> LENGTH: 10
<212> TYPE: PRT
<213> ORGANISM: Artificial
<220> FEATURE:
<223> OTHER INFORMATION: CDRH1

<400> SEQUENCE: 1

Gly Phe Thr Phe Ser Asp Tyr Asn Met Ala
1               5                   10

<210> SEQ ID NO 2
<211> LENGTH: 17
<212> TYPE: PRT
<213> ORGANISM: Artificial
<220> FEATURE:
<223> OTHER INFORMATION: CDRH2

<400> SEQUENCE: 2

Thr Ile Thr Tyr Glu Gly Arg Asn Thr Tyr Tyr Arg Asp Ser Val Lys
1               5                   10                  15

Gly

<210> SEQ ID NO 3
<211> LENGTH: 16
<212> TYPE: PRT
<213> ORGANISM: Artificial
<220> FEATURE:
<223> OTHER INFORMATION: CDRH3

<400> SEQUENCE: 3

Pro Pro Gln Tyr Tyr Glu Gly Ser Ile Tyr Arg Leu Trp Phe Ala His
1               5                   10                  15

<210> SEQ ID NO 4
<211> LENGTH: 11
<212> TYPE: PRT
<213> ORGANISM: Artificial
<220> FEATURE:
<223> OTHER INFORMATION: CDRL1

<400> SEQUENCE: 4

Arg Ala Asp Glu Ser Val Arg Thr Leu Met His
1               5                   10

<210> SEQ ID NO 5
<211> LENGTH: 7
<212> TYPE: PRT
<213> ORGANISM: Artificial
<220> FEATURE:
<223> OTHER INFORMATION: CDRL2
```

```
<400> SEQUENCE: 5

Leu Val Ser Asn Ser Glu Ile
1               5

<210> SEQ ID NO 6
<211> LENGTH: 9
<212> TYPE: PRT
<213> ORGANISM: Artificial
<220> FEATURE:
<223> OTHER INFORMATION: CDRL3

<400> SEQUENCE: 6

Gln Gln Thr Trp Ser Asp Pro Trp Thr
1               5

<210> SEQ ID NO 7
<211> LENGTH: 107
<212> TYPE: PRT
<213> ORGANISM: Artificial
<220> FEATURE:
<223> OTHER INFORMATION: Light chain variable region

<400> SEQUENCE: 7

Ala Ile Gln Leu Thr Gln Ser Pro Ser Ser Leu Ser Ala Ser Val Gly
1               5                   10                  15

Asp Arg Val Thr Ile Thr Cys Arg Ala Asp Glu Ser Val Arg Thr Leu
            20                  25                  30

Met His Trp Tyr Gln Gln Lys Pro Gly Lys Ala Pro Lys Leu Leu Ile
        35                  40                  45

Tyr Leu Val Ser Asn Ser Glu Ile Gly Val Pro Asp Arg Phe Ser Gly
    50                  55                  60

Ser Gly Ser Gly Thr Asp Phe Arg Leu Thr Ile Ser Ser Leu Gln Pro
65                  70                  75                  80

Glu Asp Phe Ala Thr Tyr Tyr Cys Gln Gln Thr Trp Ser Asp Pro Trp
                85                  90                  95

Thr Phe Gly Gln Gly Thr Lys Val Glu Ile Lys
            100                 105

<210> SEQ ID NO 8
<211> LENGTH: 321
<212> TYPE: DNA
<213> ORGANISM: Artificial Sequence
<220> FEATURE:
<223> OTHER INFORMATION: DNA encoding light chain variable region

<400> SEQUENCE: 8
gccatccagc tgacccagag cccttcctct ctcagcgcca gtgtcggaga cagagtgact      60
attacctgca gggctgacga aagcgtgaga acattgatgc actggtacca acagaagcct     120
ggcaaagccc ccaagctcct gatctatctg gtttccaatt cggagattgg agtccccgac     180
aggttcagcg gcagtgggtc tggaactgac tttcgcctga caatctcctc actccagccc     240
gaagatttcg ccacctacta ttgccagcag acttggagcg acccttggac atttggacag     300
ggcacaaaag tggagatcaa g                                                321

<210> SEQ ID NO 9
<211> LENGTH: 125
<212> TYPE: PRT
<213> ORGANISM: Artificial
<220> FEATURE:
<223> OTHER INFORMATION: Heavy chain variable region
```

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asn Met Ala Trp Val Arg Gln Ala Pro Gly Lys Gly Leu Glu Trp Val
        35                  40                  45

Ala Thr Ile Thr Tyr Glu Gly Arg Asn Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Pro Gln Tyr Tyr Glu Gly Ser Ile Tyr Arg Leu Trp Phe
            100                 105                 110

Ala His Trp Gly Gln Gly Thr Leu Val Thr Val Ser Ser
        115                 120                 125

<210> SEQ ID NO 10
<211> LENGTH: 375
<212> TYPE: DNA
<213> ORGANISM: Artificial
<220> FEATURE:
<223> OTHER INFORMATION: DNA encoding heavy chain variable region

<400> SEQUENCE: 10
gaggttcagc tcgttgaatc cggaggcgga ctcgtgcagc ctgggggctc cttgcggctg     60
agctgcgctg ccagtggctt cactttcagc gattacaata tggcctgggt cgcccaggcc    120
ccaggcaagg gtctggagtg gtggccaca attacctatg agggcagaaa cacttattac     180
cgggattcag tgaaagggcg atttaccatc agcaggata atgcaaagaa cagtctgtac     240
ctgcagatga actctctgag agctgaggac accgctgtct actattgtgc aagcccaccc    300
cagtactatg agggctcaat ctacagattg tggtttgccc attggggcca gggaacactg    360
gtgaccgtct cgagc                                                     375

<210> SEQ ID NO 11
<211> LENGTH: 214
<212> TYPE: PRT
<213> ORGANISM: Artificial
<220> FEATURE:
<223> OTHER INFORMATION: Light chain of antibody CA028_496g3

<400> SEQUENCE: 11

Ala Ile Gln Leu Thr Gln Ser Pro Ser Ser Leu Ser Ala Ser Val Gly
1               5                   10                  15

Asp Arg Val Thr Ile Thr Cys Arg Ala Asp Glu Ser Val Arg Thr Leu
            20                  25                  30

Met His Trp Tyr Gln Gln Lys Pro Gly Lys Ala Pro Lys Leu Leu Ile
        35                  40                  45

Tyr Leu Val Ser Asn Ser Glu Ile Gly Val Pro Asp Arg Phe Ser Gly
    50                  55                  60

Ser Gly Ser Gly Thr Asp Phe Arg Leu Thr Ile Ser Ser Leu Gln Pro
65                  70                  75                  80

Glu Asp Phe Ala Thr Tyr Tyr Cys Gln Gln Thr Trp Ser Asp Pro Trp
                85                  90                  95

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 234
<212> TYPE: PRT
<213> ORGANISM: Artificial
<220> FEATURE:
<223> OTHER INFORMATION: Light chain of antibody CA028_496g3 including
      signal sequence

<400> SEQUENCE: 12

Met Ser Val Pro Thr Gln Val Leu Gly Leu Leu Leu Leu Trp Leu Thr
1               5                   10                  15

Asp Ala Arg Cys Ala Ile Gln Leu Thr Gln Ser Pro Ser Ser Leu Ser
            20                  25                  30

Ala Ser Val Gly Asp Arg Val Thr Ile Thr Cys Arg Ala Asp Glu Ser
        35                  40                  45

Val Arg Thr Leu Met His Trp Tyr Gln Gln Lys Pro Gly Lys Ala Pro
    50                  55                  60

Lys Leu Leu Ile Tyr Leu Val Ser Asn Ser Glu Ile Gly Val Pro Asp
65                  70                  75                  80

Arg Phe Ser Gly Ser Gly Ser Gly Thr Asp Phe Arg Leu Thr Ile Ser
                85                  90                  95

Ser Leu Gln Pro Glu Asp Phe Ala Thr Tyr Tyr Cys Gln Gln Thr Trp
            100                 105                 110

Ser Asp Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

```
<210> SEQ ID NO 13
<211> LENGTH: 645
<212> TYPE: DNA
<213> ORGANISM: Artificial
<220> FEATURE:
<223> OTHER INFORMATION: DNA encoding Light chain of antibody
      CA028_496g3

<400> SEQUENCE: 13
gccatccagc tgacccagag cccttcctct ctcagcgcca gtgtcggaga cagagtgact      60
attacctgca gggctgacga aagcgtgaga acattgatgc actggtacca acagaagcct     120
ggcaaagccc ccaagctcct gatctatctg gtttccaatt cggagattgg agtccccgac     180
aggttcagcg gcagtgggtc tggaactgac tttcgcctga caatctcctc actccagccc     240
gaagatttcg ccacctacta ttgccagcag acttggagcg acccttggac atttggacag     300
ggcacaaaag tggagatcaa gcgtacggta gcggccccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacccctgacg    540 ctgagcaaag cagactacga aaacacaaa gtctacgcct gcgaagtcac ccatcagggc      600
ctgagctcgc ccgtcacaaa gagcttcaac aggggagagt gttag                    645

<210> SEQ ID NO 14
<211> LENGTH: 705
<212> TYPE: DNA
<213> ORGANISM: Artificial
<220> FEATURE:
<223> OTHER INFORMATION: DNA encoding Light chain of antibody
      CA028_496g3 including signal sequence

<400> SEQUENCE: 14
atgtcagttc ccacacaggt gctgggcctg cttctgttgt ggctcaccga tgctaggtgt      60
gccatccagc tgacccagag cccttcctct ctcagcgcca gtgtcggaga cagagtgact     120
attacctgca gggctgacga aagcgtgaga acattgatgc actggtacca acagaagcct     180
ggcaaagccc ccaagctcct gatctatctg gtttccaatt cggagattgg agtccccgac     240
aggttcagcg gcagtgggtc tggaactgac tttcgcctga caatctcctc actccagccc     300
gaagatttcg ccacctacta ttgccagcag acttggagcg acccttggac atttggacag     360
ggcacaaaag tggagatcaa gcgtacggta gcggccccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag cacccctgacg    600 ctgagcaaag cagactacga aaacacaaa gtctacgcct gcgaagtcac ccatcagggc      660
ctgagctcgc ccgtcacaaa gagcttcaac aggggagagt gttag                    705

<210> SEQ ID NO 15
<211> LENGTH: 455
<212> TYPE: PRT
<213> ORGANISM: Artificial
<220> FEATURE:
<223> OTHER INFORMATION: Heavy chain of antibody CA028_496g3

<400> SEQUENCE: 15
```

-continued

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Asp Tyr
            20                  25                  30
Asn Met Ala Trp Val Arg Gln Ala Pro Gly Lys Gly Leu Glu Trp Val
         35                  40                  45
Ala Thr Ile Thr Tyr Glu Gly Arg Asn Thr Tyr Tyr Arg Asp Ser Val
     50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
             85                  90                  95
Ala Ser Pro Pro Gln Tyr Tyr Glu Gly Ser Ile Tyr Arg Leu Trp Phe
         100                 105                 110
Ala His Trp Gly Gln Gly Thr Leu Val Thr Val Ser Ser Ala Ser Thr
     115                 120                 125
Lys Gly Pro Ser Val Phe Pro Leu Ala Pro Ser Ser Lys Ser Thr Ser
130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
             165                 170                 175
Thr Phe Pro Ala Val Leu Gln Ser Ser Gly Leu Tyr Ser Leu Ser Ser
         180                 185                 190
Val Val Thr Val Pro Ser Ser Ser Leu Gly Thr Gln Thr Tyr Ile Cys
     195                 200                 205
Asn Val Asn His Lys Pro Ser Asn Thr Lys Val Asp Lys Lys Val Glu
210                 215                 220
Pro Lys Ser Cys Asp Lys Thr His Thr Cys Pro Pro Cys Pro Ala Pro
225                 230                 235                 240
Glu Leu Leu Gly Gly Pro Ser Val Phe Leu Phe Pro Pro Lys Pro Lys
             245                 250                 255
Asp Thr Leu Met Ile Ser Arg Thr Pro Glu Val Thr Cys Val Val Val
         260                 265                 270
Asp Val Ser His Glu Asp Pro Glu Val Lys Phe Asn Trp Tyr Val Asp
     275                 280                 285
Gly Val Glu Val His Asn Ala Lys Thr Lys Pro Arg Glu Glu Gln Tyr
290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
             325                 330                 335
Pro Ala Pro Ile Glu Lys Thr Ile Ser Lys Ala Lys Gly Gln Pro Arg
         340                 345                 350
Glu Pro Gln Val Tyr Thr Leu Pro Pro Ser Arg Asp Glu Leu Thr Lys
     355                 360                 365
Asn Gln Val Ser Leu Thr Cys Leu Val Lys Gly Phe Tyr Pro Ser Asp
370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
             405                 410                 415
Lys Leu Thr Val Asp Lys Ser Arg Trp Gln Gln Gly Asn Val Phe Ser
```

Cys Ser Val Met His Glu Ala Leu His Asn His Tyr Thr Gln Lys Ser
                435                 440                 445
Leu Ser Leu Ser Pro Gly Lys
    450                 455

<210> SEQ ID NO 16
<211> LENGTH: 474
<212> TYPE: PRT
<213> ORGANISM: Artificial
<220> FEATURE:
<223> OTHER INFORMATION: Heavy chain of antibody CA028_496g3 including
      signal sequence

<400> SEQUENCE: 16

Met Glu Trp Ser Trp Val Phe Leu Phe Phe Leu Ser Val Thr Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asp Tyr Asn Met Ala Trp Val Arg Gln Ala Pro Gly Lys Gly Leu
    50                  55                  60

Glu Trp Val Ala Thr Ile Thr Tyr Glu Gly Arg Asn Thr Tyr Tyr Arg
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Ser Pro Pro Gln Tyr Tyr Glu Gly Ser Ile Tyr Arg
        115                 120                 125

Leu Trp Phe Ala His Trp Gly Gln Gly Thr Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 17
<211> LENGTH: 1365
<212> TYPE: DNA
<213> ORGANISM: Artificial
<220> FEATURE:
<223> OTHER INFORMATION: DNA (including exons) encoding heavy chain of
      antibody CA028_496g3

<400> SEQUENCE: 17
gaggttcagc tcgttgaatc cggaggcgga ctcgtgcagc ctgggggctc cttgcggctg      60
agctgcgctg ccagtggctt cactttcagc gattacaata tggcctgggt cgcgcaggcc     120
ccaggcaagg gtctggagtg ggtggccaca attacctatg agggcagaaa cacttattac     180
cgggattcag tgaaagggcg atttaccatc agcagggata tgcaaagaa cagtctgtac      240 ctgcagatga actctctgag agctgaggac accgctgtct actattgtgc aagcccaccc     300
cagtactatg agggctcaat ctacagattg tggtttgccc attggggcca gggaacactg     360
gtgaccgtct cgagcgcttc tacaaagggc ccatcggtct tccccctggc accctcctcc     420
aagagcacct ctgggggcac agcggccctg gctgcctgg tcaaggacta cttccccgaa      480
ccggtgacgg tgtcgtggaa ctcaggcgcc ctgaccagcg gcgtgcacac cttcccggct     540
gtcctacagt cctcaggact ctactccctc agcagcgtgg tgaccgtgcc ctccagcagc     600
ttgggcaccc agacctacat ctgcaacgtg aatcacaagc ccagcaacac caaggtcgac     660
aagaaagttg agcccaaatc ttgtgacaaa actcacacat gcccaccgtg cccagcacct     720
gaactcctgg ggggaccgtc agtcttcctc ttccccccaa aacccaagga caccctcatg     780
atctcccgga cccctgaggt cacatgcgtg gtggtggacg tgagccacga agaccctgag     840
gtcaagttca actggtacgt ggacggcgtg gaggtgcata atgccaagac aaagccgcgg     900
gaggagcagt acaacagcac gtaccgtgtg gtcagcgtcc tcaccgtcct gcaccaggac     960
tggctgaatg gcaaggagta caagtgcaag gtctccaaca aagccctccc agcccccatc    1020
gagaaaacca tctccaaagc caaagcgcag ccccgagaac cacaggtgta caccctgccc    1080
ccatcccggg atgagctgac caagaaccag gtcagcctga cctgcctggt caaaggcttc    1140

```
tatcccagcg acatcgccgt ggagtgggag agcaatgggc agccggagaa caactacaag    1200
accacgcctc ccgtgctgga ctccgacggc tccttcttcc tctacagcaa gctcaccgtg    1260
gacaagagca ggtggcagca ggggaacgtc ttctcatgct ccgtgatgca tgaggctctg    1320
cacaaccact acacgcagaa gagcctctcc ctgtctccgg gtaaa                    1365

<210> SEQ ID NO 18
<211> LENGTH: 1422
<212> TYPE: DNA
<213> ORGANISM: Artificial
<220> FEATURE:
<223> OTHER INFORMATION: DNA (including exons) encoding heavy chain of
      antibody CA028_496g3 with signal sequence

<400> SEQUENCE: 18
atggaatggt cctgggtctt cctgttttc ctttctgtca caaccggggt gcacagcgag      60
gttcagctcg ttgaatccgg aggcggactc gtgcagcctg ggggctcctt gcggctgagc    120
tgcgctgcca gtggcttcac tttcagcgat tacaatatgg cctgggtgcg ccaggccccga   180 ggcaagggtc tggagtgggt ggccacaatt acctatgagg cagaaacac ttattaccgg     240 gattcagtga aagggcgatt taccatcagc agggataatg caaagaacag tctgtacctg    300
cagatgaact ctctgagagc tgaggacacc gctgtctact attgtgcaag cccacccag     360 tactatgagg gctcaatcta cagattgtgg tttgcccatt ggggccaggg aacactggtg    420
accgtctcga gcgcttctac aaagggccca tcggtcttcc cctggcacc ctcctccaag     480 agcacctctg ggggcacagc ggccctgggc tgcctggtca aggactactt ccccgaaccg    540
gtgacggtgt cgtggaactc aggcgccctg accagcggcg tgcacacctt cccggctgtc    600
ctacagtcct caggactcta ctccctcagc agcgtggtga ccgtgccctc agcagcttg     660 ggcacccaga cctacatctg caacgtgaat cacaagccca gcaaccacaa ggtcgacaag    720
aaagttgagc ccaaatcttg tgacaaaact cacacatgcc caccgtgccc agcacctgaa    780
ctcctggggg gaccgtcagt cttcctcttc cccccaaaac ccaaggacac cctcatgatc    840
tcccggaccc ctgaggtcac atgcgtggtg gtggacgtga gccacgaaga ccctgaggtc    900
aagttcaact ggtacgtgga cggcgtggag gtgcataatg ccaagacaaa gccgcgggag    960
gagcagtaca acagcacgta ccgtgtggtc agcgtcctca ccgtcctgca ccaggactgg   1020
ctgaatggca aggagtacaa gtgcaaggtc tccaacaaag ccctcccagc ccccatcgag   1080
aaaaccatct ccaaagccaa agcgcagccc cgagaaccac aggtgtacac cctgccccca   1140
tcccgggatg agctgaccaa gaaccaggtc agcctgacct gcctggtcaa aggcttctat   1200
cccagcgaca tcgccgtgga gtgggagagc aatgggcagc cggagaacaa ctacaagacc   1260
acgcctcccg tgctgactc cgacggctcc ttcttcctct acagcaagct caccgtggac   1320
aagagcaggt ggcagcaggg gaacgtcttc tcatgctccg tgatgcatga ggctctgcac   1380
aaccactaca cgcagaagag cctctccctg tctccgggta aa                      1422

<210> SEQ ID NO 19
<211> LENGTH: 1422
<212> TYPE: DNA
<213> ORGANISM: Artificial
<220> FEATURE:
<223> OTHER INFORMATION: cDNA encoding heavy chain of antibody
      CA028_496g3 including signal sequence

<400> SEQUENCE: 19
atggaatggt cctgggtctt cctgttttc ctttctgtca caaccggggt gcacagcgag     60
```

-continued

```
gttcagctcg ttgaatccgg aggcggactc gtgcagcctg ggggctcctt gcggctgagc    120
tgcgctgcca gtggcttcac tttcagcgat tacaatatgg cctgggtgcg ccaggcccca    180
ggcaagggtc tggagtgggt ggccacaatt acctatgagg gcagaaacac ttattaccgg    240
gattcagtga aagggcgatt taccatcagc agggataatg caaagaacag tctgtacctg    300
cagatgaact ctctgagagc tgaggacacc gctgtctact attgtgcaag cccaccccag    360
tactatgagg gctcaatcta cagattgtgg tttgcccatt ggggccaggg aacactggtg    420
accgtctcga gcgcttctac aaagggccca tcggtcttcc cctggcacc ctcctccaag     480 agcacctctg ggggcacagc ggccctgggc tgcctggtca aggactactt ccccgaaccg    540
gtgacggtgt cgtggaactc aggcgccctg accagcggcg tgcacacctt cccggctgtc    600
ctacagtcct caggactcta ctccctcagc agcgtggtga ccgtgccctc cagcagcttg    660
ggcacccaga cctacatctg caacgtgaat cacaagccca gcaacaccaa ggtcgacaag    720
aaagttgagc ccaaatcttg tgacaaaact cacacatgcc caccgtgccc agcacctgaa    780
ctcctggggg gaccgtcagt cttcctcttc cccccaaaac ccaaggacac cctcatgatc    840
tcccggaccc ctgaggtcac atgcgtggtg gtggacgtga gccacgaaga ccctgaggtc    900
aagttcaact ggtacgtgga cggcgtggag gtgcataatg ccaagacaaa gccgcgggag    960
gagcagtaca acagcacgta ccgtgtggtc agcgtcctca ccgtcctgca ccaggactgg   1020
ctgaatggca aggagtacaa gtgcaaggtc tccaacaaag ccctcccagc ccccatcgag   1080
aaaaccatct ccaaagccaa agcgcagccc cgagaaccac aggtgtacac cctgccccca   1140
tcccgggatg agctgaccaa gaaccaggtc agcctgacct gcctggtcaa aggcttctat   1200
cccagcgaca tcgccgtgga gtgggagagc aatgggcagc cggagaacaa ctacaagacc   1260
acgcctcccg tgctggactc cgacggctcc ttcttcctct acagcaagct caccgtggac   1320
aagagcaggt ggcagcaggg gaacgtcttc tcatgctccg tgatgcatga ggctctgcac   1380
aaccactaca cgcagaagag cctctccctg tctccgggta aa                      1422
```